US010631810B2

(12) United States Patent
Arai et al.

(10) Patent No.: US 10,631,810 B2
(45) Date of Patent: Apr. 28, 2020

(54) IMAGE PROCESSING DEVICE, RADIATION IMAGING SYSTEM, IMAGE PROCESSING METHOD, AND IMAGE PROCESSING PROGRAM

(71) Applicant: FUJIFILM Corporation, Tokyo (JP)

(72) Inventors: Takahisa Arai, Ashigarakami-gun (JP); Tomoki Inoue, Ashigarakami-gun (JP); Takeshi Okubo, Ashigarakami-gun (JP)

(73) Assignee: FUJIFILM Corporation, Minato-Ku, Tokyo (JP)

( * ) Notice: Subject to any disclaimer, the term of this patent is extended or adjusted under 35 U.S.C. 154(b) by 292 days.

(21) Appl. No.: 15/896,138

(22) Filed: Feb. 14, 2018

(65) Prior Publication Data
US 2018/0185000 A1    Jul. 5, 2018

Related U.S. Application Data

(63) Continuation of application No. PCT/JP2016/056573, filed on Mar. 3, 2016.

(30) Foreign Application Priority Data

Sep. 10, 2015  (JP) ................................ 2015-178716

(51) Int. Cl.
*A61B 6/04*    (2006.01)
*A61B 6/00*    (2006.01)
(Continued)

(52) U.S. Cl.
CPC .............. *A61B 6/502* (2013.01); *A61B 6/025* (2013.01); *A61B 6/032* (2013.01); *A61B 6/0414* (2013.01);
(Continued)

(58) Field of Classification Search
CPC ...... A61B 6/032; A61B 6/4441; A61B 6/4447; A61B 6/04
See application file for complete search history.

(56) References Cited

U.S. PATENT DOCUMENTS 9,668,711 B2 * 6/2017 Smith .................... A61B 6/025
2001/0038707 A1  11/2001 Ohara
(Continued)

FOREIGN PATENT DOCUMENTS

JP    2001-299733 A    10/2001
JP    2007-260187 A    10/2007
(Continued)

OTHER PUBLICATIONS

International Search Report for PCT/JP2016/056573, dated May 24, 2016.
(Continued)

*Primary Examiner* — Don K Wong
(74) *Attorney, Agent, or Firm* — Sughrue Mion, PLLC

(57) ABSTRACT

A control unit sets an angle of incidence of radiation, incident on a detection surface of a radiation detector with respect to the detection surface, to a plurality of angles different from each other including an angle (0 degrees) in a normal direction of the detection surface, and acquires at least one of a plurality of projection images captured by the radiation detector in accordance with the angle of incidence or reconstructed images reconstructed using the projection images. In addition, the control unit generates a first synthetic mammogram image on the basis of the one image. In addition, the control unit 40 generates a second synthetic mammogram image by synthesizing a high-frequency image having a high-frequency component higher than a predetermined frequency of the first synthetic mammogram image and a low-frequency image having a low-frequency com-
(Continued)

ponent of equal to or lower than a predetermined frequency of a zero-degree projection image.

20 Claims, 11 Drawing Sheets

(51) Int. Cl.
    *G06T 11/00*     (2006.01)
    *A61B 6/02*     (2006.01)
    *A61B 6/03*     (2006.01)

(52) U.S. Cl.
    CPC .......... *A61B 6/5211* (2013.01); *A61B 6/5223* (2013.01); *A61B 6/54* (2013.01); *G06T 11/005* (2013.01); *G06T 11/006* (2013.01); *G06T 11/008* (2013.01); *G06T 2210/41* (2013.01); *G06T 2211/421* (2013.01)

(56) References Cited

U.S. PATENT DOCUMENTS

| | | |
|---|---|---|
| 2009/0123052 A1 | 5/2009 | Ruth et al. |
| 2011/0142317 A1 | 6/2011 | Riddell |
| 2014/0093029 A1 | 4/2014 | Masumoto et al. |
| 2014/0327702 A1 | 11/2014 | Kreeger et al. |

FOREIGN PATENT DOCUMENTS

| | | |
|---|---|---|
| JP | 2011-125698 A | 6/2011 |
| JP | 2012-245329 A | 12/2012 |
| JP | 2014-068752 A | 4/2014 |
| JP | 2014-128716 A | 7/2014 |
| JP | 2014-534042 A | 12/2014 |
| WO | 2013078476 A1 | 5/2013 |
| WO | 2015054518 A1 | 4/2015 |
| WO | 2015130916 A1 | 9/2015 |

OTHER PUBLICATIONS

Written Opinion of the International Searching Authority dated May 24, 2016, in counterpart International Application No. PCT/JP2016/056573.

International Preliminary Report on Patentability dated Mar. 13, 2018, in counterpart International Application No. PCT/JP2016/056573.

Communication dated Jul. 18, 2018, from the European Patent Office in counterpart European Application No. 16843972.7.

* cited by examiner

IMAGE PROCESSING DEVICE, RADIATION IMAGING SYSTEM, IMAGE PROCESSING METHOD, AND IMAGE PROCESSING PROGRAM

CROSS-REFERENCE TO RELATED APPLICATIONS

This application is a Continuation of PCT International Application No. PCT/JP2016/056573 filed on Mar. 3, 2016, which claims priority under 35 U.S.C § 119(a) to Japanese Patent Application No. 2015-178716 filed on Sep. 10, 2015. Each of the above application(s) is hereby expressly incorporated by reference, in its entirety, into the present application.

BACKGROUND OF THE INVENTION

1. Field of the Invention

The present invention relates to an image processing device, a radiation imaging system, an image processing method, and a non-transitory computer readable recording medium storing an image processing program.

2. Description of the Related Art

Generally, there are known radiation imaging devices that perform radiation imaging aiming at medical diagnoses or the like. As this kind of radiation imaging device, a technique is known for irradiating a subject with radiation by making the angle of incidence of radiation on the radiation detection surface of a radiation detector different from each other within a predetermined range, and performing tomosynthesis imaging for capturing radiation images (projection images) at the respective angles of incidence.

In addition, there is an image processing technique for generating various radiation images using a plurality of projection images obtained by tomosynthesis imaging.

As this kind image processing technique, JP2012-245329A discloses a technique for overlay-displaying a two-dimensional image on a target region of a reconstructed image reconstructed from the projection image. In addition, JP2007-260187A discloses a technique for generating a third reconstructed image on the basis of a first reconstructed image obtained by performing a two-dimensional back projection process on the basis of projection images, and a second reconstructed image obtained by performing a three-dimensional back projection process on the basis of the projection images.

SUMMARY OF THE INVENTION

On the other hand, there is a maximum intensity projection (MIP) method as a technique for generating a synthetic mammogram image which is a pseudo two-dimensional image from each projection image or a reconstructed image reconstructed from each projection image. The MIP method is a method in which a projection process is performed on three-dimensionally constructed data in any viewpoint direction, and the maximum value of pixel values in a projection path is set to a pixel value on a projection surface. A synthetic mammogram image generated using the MIP method is not likely to be influenced by noise, and thus can be distinctly depicted even in an image having a small contrast.

On the other hand, in the MIP method, since a pixel having a maximum pixel value is used, a synthetic mammogram image is generated using information of a structure which is not present on the same cross-section, and thus information of a pixel value between pixels may be lost. As a result, the image quality of the synthetic mammogram image may deteriorate.

The present invention is contrived in consideration of the above fact, and an object thereof is to provide an image processing device, a radiation imaging system, an image processing method, and a non-transitory computer readable recording medium storing an image processing program which are capable of improving the image quality of a synthetic mammogram image.

In order to achieve the above object, according to the present invention, there is provided an image processing device comprising: an acquisition unit that sets an angle of incidence of radiation, which is emitted from a radiation source, is transmitted through a subject, and is incident on a detection surface of a radiation detector with respect to the detection surface, to a plurality of angles different from each other including an angle in a normal direction of the detection surface, and acquires at least one of a plurality of projection images captured by the radiation detector in accordance with the angle of incidence or reconstructed images reconstructed using the projection images; a first generation unit that generates a first synthetic mammogram image on the basis of any one of the plurality of the projection images or the reconstructed images; and a second generation unit that generates a second synthetic mammogram image by synthesizing an image having a high-frequency component higher than a first spatial frequency of the first synthetic mammogram image and an image having a low-frequency component of equal to or lower than a second spatial frequency of a projection image, the projection image is one of the plurality of the projection images and captured with the angle of incidence set to be in the normal direction.

In the image processing device of the present invention the second generation unit may synthesize the second synthetic mammogram image and the first synthetic mammogram image.

The image processing device of the present invention may further comprise a receiving unit that receives a type of image obtained by synthesis, and in a case where the type of image received by the receiving unit is a calcification reading image or a high-frequency component enhanced image, the second generation unit may further synthesize the second synthetic mammogram image and the first synthetic mammogram image.

In the image processing device of the present invention, the second generation unit may further synthesize the second synthetic mammogram image and the projection image captured with the angle of incidence set to be in the normal direction.

The image processing device of the present invention may further comprise a receiving unit that receives a type of image obtained by synthesis, and in a case where the type of image received by the receiving unit is a tumor reading image or a low-frequency component enhanced image, the second generation unit may further synthesize the second synthetic mammogram image and the projection image captured with the angle of incidence set to be in the normal direction.

In the image processing device of the present invention, the second generation unit may perform the synthesis by performing weighting on each of an image having a high-frequency component of the first synthetic mammogram image and an image having a low-frequency component of the projection image.

The image processing device of the present invention may further comprise a frequency receiving unit that receives an input of information for specifying at least one of the first spatial frequency or the second spatial frequency.

In the image processing device of the present invention, the first spatial frequency may be lower than the second spatial frequency, or the first spatial frequency and the second spatial frequency may be equal to each other.

In addition, according to the present invention, there is provided a radiation imaging system comprising: a radiation imaging device including a radiation source and a radiation detector provided on an opposite side to the radiation source with a subject interposed therebetween; and the image processing device of the present invention.

In addition, according to the present invention, there is provided an image processing method comprising causing a computer to execute: setting an angle of incidence of radiation, which is emitted from a radiation source, is transmitted through a subject, and is incident on a detection surface of a radiation detector with respect to the detection surface, to a plurality of angles different from each other including an angle in a normal direction of the detection surface, and acquiring at least one of a plurality of projection images captured by the radiation detector in accordance with the angle of incidence or reconstructed images reconstructed using the projection images; generating a first synthetic mammogram image on the basis of any one of the plurality of the projection images or the reconstructed images; and generating a second synthetic mammogram image by synthesizing an image having a high-frequency component higher than a first spatial frequency of the first synthetic mammogram image and an image having a low-frequency component of equal to or lower than a second spatial frequency of a projection image, the projection image is one of the plurality of the projection images and captured with the angle of incidence set to be in the normal direction.

In addition, according to the present invention, there is provided a non-transitory computer readable recording medium storing an image processing program for causing a computer to execute: setting an angle of incidence of radiation, which is emitted from a radiation source, is transmitted through a subject, and is incident on a detection surface of a radiation detector with respect to the detection surface, to a plurality of angles different from each other including an angle in a normal direction of the detection surface, and acquiring at least one of a plurality of projection images captured by the radiation detector in accordance with the angle of incidence or reconstructed images reconstructed using the projection images; generating a first synthetic mammogram image on the basis any one of the plurality of the projection images or the reconstructed images; and generating a second synthetic mammogram image by synthesizing an image having a high-frequency component higher than a first spatial frequency of the first synthetic mammogram image and an image having a low-frequency component of equal to or lower than a second spatial frequency of a projection image, the projection image is one of the plurality of the projection images and captured with the angle of incidence set to be in the normal direction.

In the present invention, it is possible to provide an image processing device, a radiation imaging system, an image processing method, and a non-transitory computer readable recording medium storing an image processing program which are capable of improving the image quality of a synthetic mammogram image.

DESCRIPTION OF THE PREFERRED EMBODIMENTS

Hereinafter, embodiments of the present invention will be described in detail with reference to the accompanying drawings. Meanwhile, the present embodiments do not limit the present invention.

First Embodiment

Figure 1:
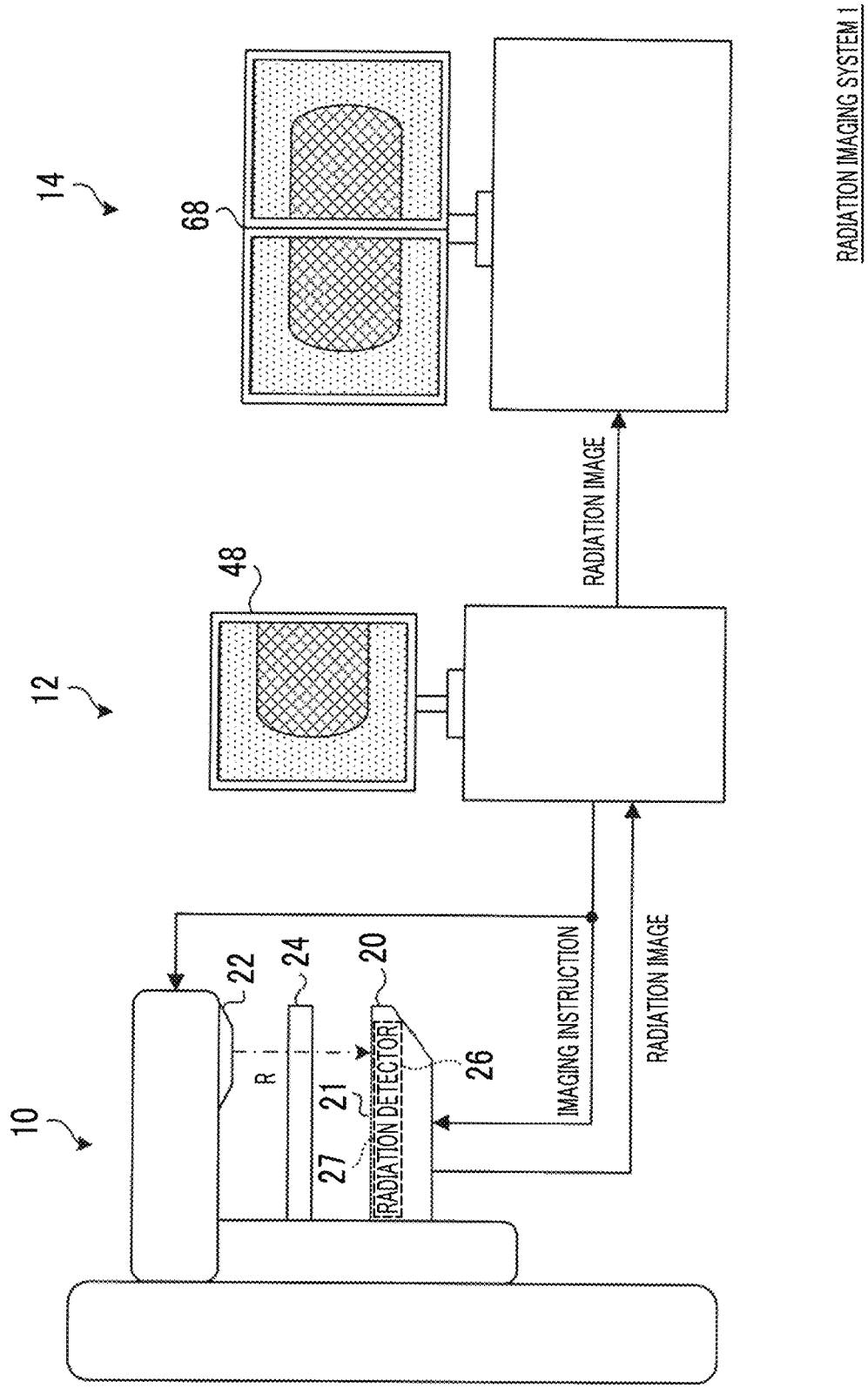
FIG. 1 is a configuration diagram illustrating an example of the entire configuration of a radiation imaging system according to a first embodiment.

First, the entire configuration of a radiation imaging system according to the present embodiment will be described with reference to FIG. 1.

A radiation imaging system 1 of the present embodiment includes a radiation imaging device 10, a console 12, and a radiation image reading device 14. In the present embodiment, a case will be described in which the console 12 functions as an example of an image processing device of the present invention.

The radiation imaging system 1 of the present embodiment is configured such that the radiation imaging device 10 captures a radiation image on the basis of an imaging instruction performed from the console 12.

The radiation imaging device 10 of the present embodiment is a device that captures an image of an examinee's breast, as a subject, using radiation R (for example, X-rays) in a standing state where the examinee stands or a seated state where the examinee sits on a chair (inclusive of a wheelchair) or the like. A specific example of the radiation imaging device 10 includes mammography.

An imaging surface 21 with which an examinee's breast comes into contact is formed of, for example, carbon from the viewpoint of the transmissivity or intensity of the radiation R. A radiation detector 26 that detects the radiation R having passed through the breast and imaging surface 21 is disposed inside an imaging table 20. A radiation image is generated on the basis of the radiation R detected by the radiation detector 26. The type of radiation detector 26 of the present embodiment is not particularly limited, and may be, for example, a radiation detector of an indirect conversion type in which the radiation R is converted into light and the converted light is converted into electric charge, or may be a radiation detector of a direct conversion type in which the radiation R is directly converted into electric charge.

The radiation imaging device 10 is provided with a radiation source 22 so as to face the imaging surface 21 of the imaging table 20, and emits the radiation R from the radiation source 22 toward the imaging surface 21.

In a case where a radiation image of an examinee's breast is captured, one breast which is a subject is fixed by using a compression plate 24 provided between the radiation source 22 and the imaging surface 21 of the imaging table 20 to perform compression between imaging surface 21 and the compression plate 24, and the radiation R is emitted to the fixed breast from the radiation source 22. Meanwhile, the compression plate 24 has a member that transmits the radiation R used therein.

Figure 2:
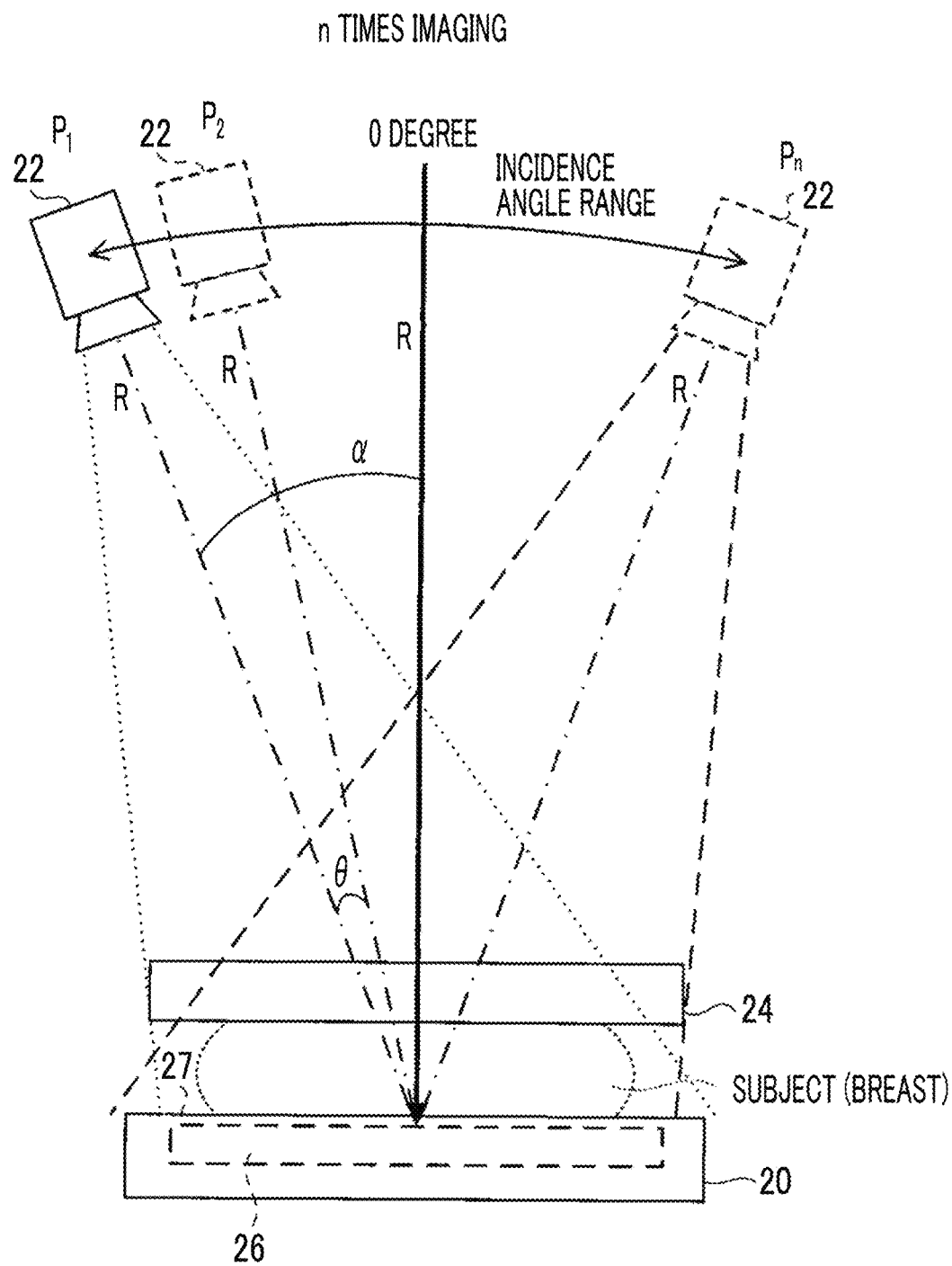
FIG. 2 is a diagram illustrating tomosynthesis imaging in a radiation imaging device according to the first embodiment.

As shown in FIG. 2, the radiation imaging device 10 of the present embodiment can irradiate a subject with the radiation R by making the angles of incidence of the radiation R emitted from the radiation source 22 different from each other within a predetermined range, and perform imaging (so-called tomosynthesis imaging) for each of the different angles of incidence. The "angle of incidence" as used herein refers to an angle between the normal line of a detection surface 27 of the radiation detector 26 and a radiation axis. Therefore, in a case where the normal line and the radiation axis are coincident with each other, the angle of incidence is set to 0 degrees. In addition, herein, the detection surface 27 of the radiation detector 26 is set to a surface substantially parallel to the imaging surface 21. A specific example of a range in which the angles of incidence in one-time tomosynthesis imaging are made different from each other includes a range of ±10 degrees or ±20 degrees with respect to the normal line of the detection surface 27 of the radiation detector 26, and the like. Meanwhile, each radiation image captured by tomosynthesis imaging refers to a "projection image".

Meanwhile, in the present embodiment, as shown in FIG. 2, the radiation source 22 is sequentially moved to imaging positions where the angle of incidence decreases every predetermined angle θ from an angle at which the angle of incidence of the radiation R is set to an angle α, and imaging is performed at n positions (imaging positions) of $P_1$ to $P_n$ where the radiation source 22 is located.

In the present embodiment, the radiation image such as a projection image captured by the radiation detector 26 of the radiation imaging device 10 is transmitted to the console 12. The console 12 of the present embodiment controls the radiation imaging device 10 using an imaging menu, other various types of information and the like acquired from an external system (for example, radiology information system (RIS)) or the like through a wireless communication local area network (LAN) or the like. In addition, the console 12 of the present embodiment transmits and receives various types of information to and from the radiation detector 26 of the radiation imaging device 10. In addition, the console 12 of the present embodiment generates various types of radiation images such as a synthetic mammogram image and displays the generated images on a display unit 48, on the basis of a reconstructed image reconstructed from the projection image or the projection image captured by the radiation imaging device 10. Meanwhile, in the present embodiment, the "reconstructed image" is an image which is generated by reconstructing a projection image Tp, and is also called a tomographic image. Meanwhile, a method of generating a reconstructed image is not particularly limited, and well-known reconstruction methods can be used. As a specific example of the method of generating a reconstructed image, a well-known computed tomography (CT) reconstruction method can be exemplified in addition to a shift-and-add method. For example, as the CT reconstruction method, a filtered back projection (FBP) method which is a representative method can be exemplified. The FBP method is a reconstruction method in which plane parallel type tomographic scanning which is tomography is considered as a portion of cone-beam CT scanning and the filtered back projection method is extended. Further, as the reconstruction method, a repeated reconstruction method disclosed in JP2011-125698A can also be used. This repeated reconstruction method is also a CT reconstruction method, but can also be applied to the reconstruction of the projection image Tp, similarly to the FBP method.

Further, the console 12 of the present embodiment transmits the radiation image such as a projection image acquired from the radiation detector 26 or various types of radiation images generated, to the radiation image reading device 14.

In addition, the radiation image reading device 14 of the present embodiment has a function of receiving a radiation image or the like from the console 12, and displaying the received radiation image or the like on a display unit 68. A specific example of the radiation image reading device 14 includes a so-called viewer or the like, but is not particularly limited, and may be a portable information terminal device such as a tablet terminal, a smartphone, a personal digital assistance (PDA), and the like.

Figure 3:
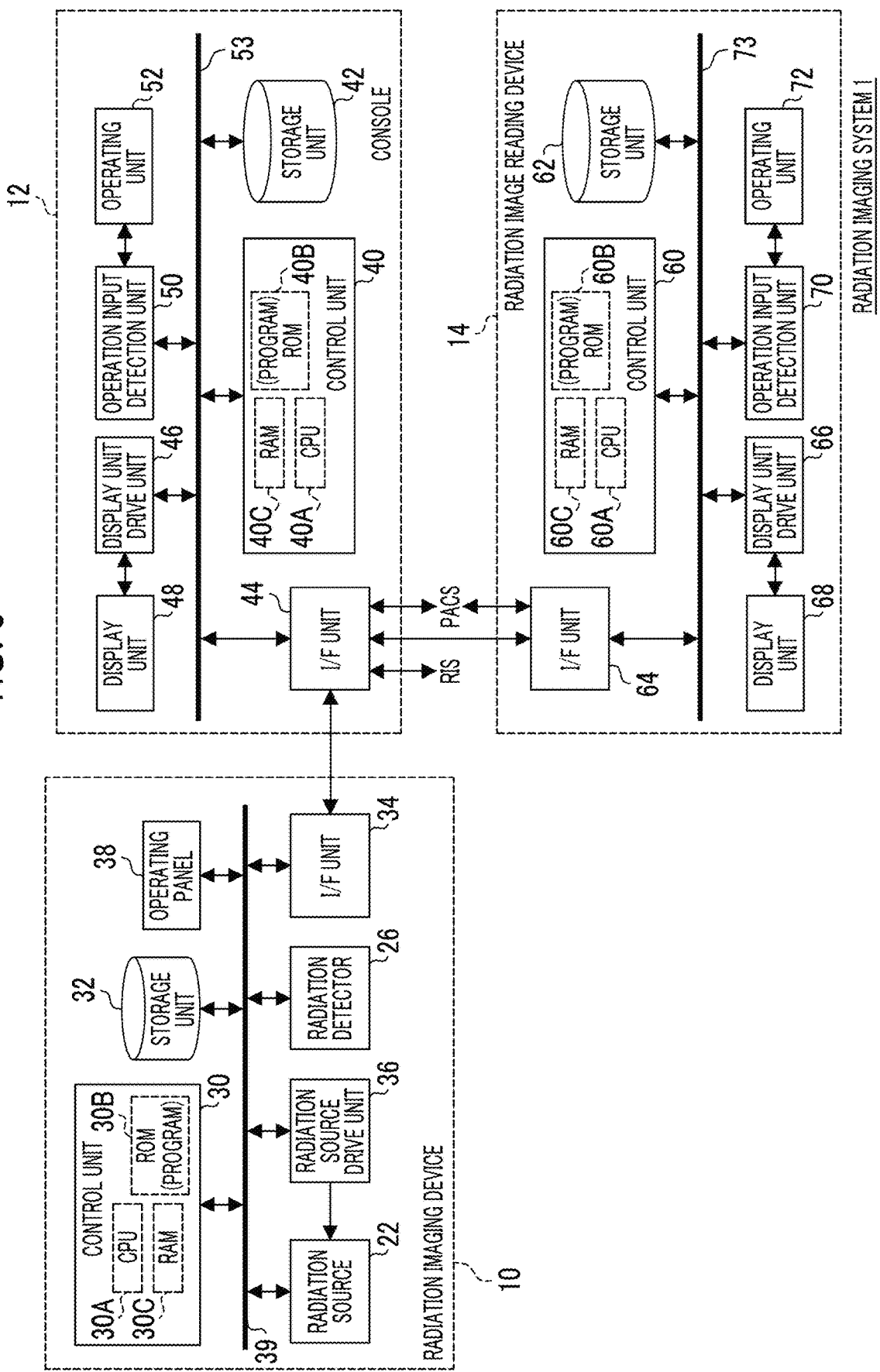
FIG. 3 is a block diagram illustrating an example of the configuration of the radiation imaging system according to the first embodiment.

FIG. 3 shows a block diagram illustrating an example of the configuration of the radiation imaging system 1 of the present embodiment.

The radiation imaging device 10 of the present embodiment includes a radiation source 22, a radiation detector 26, a control unit 30, a storage unit 32, an interface (I/F) unit 34, a radiation source drive unit 36, and an operating panel 38.

The radiation source 22, the radiation detector 26, the control unit 30, the storage unit 32, the I/F unit 34, the radiation source drive unit 36, and the operating panel 38 are connected to each other so as to be capable of mutually exchanging various types of information through a bus 39 such as a system bus or a control bus.

The control unit 30 of the present embodiment controls the entire operation of the radiation imaging device 10. In addition, the control unit 30 of the present embodiment controls the radiation source 22 and the radiation detector 26 in a case where a radiation image is captured. The control unit 30 of the present embodiment includes a central processing unit (CPU) 30A, a read only memory (ROM) 30B, and a random access memory (RAM) 30C. The ROM 30B has various types of programs or the like executed by the CPU 30A stored therein in advance. The RAM 30C temporarily stores various types of data.

The storage unit 32 has a radiation image captured by the radiation detector 26, other various types of information and the like stored therein. A specific example of the storage unit 32 includes a hard disk drive (HDD), a solid state drive (SSD), or the like.

The I/F unit 34 performs communication of various types of information with the console 12 through wireless communication or cable communication.

The radiation source drive unit 36 moves the radiation source 22 to an imaging position according to the angle of incidence of the radiation R.

The operating panel 38 is provided with a function of receiving an instruction (such as, for example, a compression instruction for a breast using the compression plate 24) relating to imaging performed by a user. The operating panel 38 is provided on, for example, the imaging table 20 of the radiation imaging device 10. Meanwhile, the operating panel 38 may be provided as a touch panel. Meanwhile, in the present embodiment, a "user" refers to an engineer, a doctor or the like who performs imaging using the radiation imaging system 1 (radiation imaging device 10).

On the other hand, the console 12 of the present embodiment is a server computer. As shown in FIG. 3, the console 12 includes a control unit 40, a storage unit 42, an I/F unit 44, a display unit drive unit 46, a display unit 48, an operation input detection unit 50, and an operating unit 52. The control unit 40, the storage unit 42, the I/F unit 44, the display unit drive unit 46, and the operation input detection unit 50 are connected to each other so as to be capable of mutually exchanging various types of information through a bus 53 such as a system bus or a control bus.

The control unit 40 of the present embodiment controls the entire operation of the console 12. The control unit 40 of the present embodiment includes a CPU 40A, a ROM 40B, and a RAM 40C. The ROM 40B has various types of programs or the like stored therein in advance which include an image processing program, described later, executed by the CPU 40A. The RAM 40C temporarily stores various types of data. In the radiation imaging system 1 of the present embodiment, the CPU 40A executes an image processing program stored in the ROM 40B, whereby the control unit 40 functions as an example of an acquisition unit, a first generation unit, a second generation unit, and a receiving unit of the present invention.

The storage unit 42 has a radiation image captured by the radiation imaging device 10, other various types of information and the like stored therein. A specific example of the storage unit 42 includes a HDD, a SSD or the like.

The I/F unit 44 performs communication of various types of information with the radiation imaging device 10, the radiation image reading device 14, an external system such as a RIS or a picture archiving and communication system (PACS), and the like through wireless communication or cable communication.

The display unit 48 displays various types of information. The display unit drive unit 46 controls display of various types of information on the display unit 48.

The operating unit 52 is used in order for a user to input an instruction relating to capturing of a radiation image including an instruction for exposing the radiation R, various types of information, or the like.

The operating unit 52 is not particularly limited, and examples of the operating unit include various types of switches, a touch panel, a touch pen, a mouse, and the like. Meanwhile, the operating unit 52 and the display unit 48 may be integrated with each other to form a touch panel display. The operation input detection unit 50 detects an operation state for the operating unit 52.

On the other hand, the radiation image reading device 14 of the present embodiment includes a control unit 60, a storage unit 62, an I/F unit 64, a display unit drive unit 66, a display unit 68, an operation input detection unit 70, and an operating unit 72. The control unit 60, the storage unit 62, the I/F unit 64, the display unit drive unit 66, and the operation input detection unit 70 are connected to each other so as to be capable of mutually exchanging various types of information through a bus 73 such as a system bus or a control bus.

The control unit 60 of the present embodiment controls the entire operation of the radiation image reading device 14. The control unit 60 of the present embodiment includes a CPU 60A, a ROM 60B, and a RAM 60C. The ROM 60B has various types of programs or the like executed by the CPU 60A stored therein in advance. The RAM 60C temporarily stores various types of data.

The storage unit 62 has a radiation image received from the console 12, other various types of information or the like stored therein. A specific example of the storage unit 62 includes a HDD, a SSD or the like.

The I/F unit 64 performs communication of various types of information with the console 12, an external system such as a PACS, and the like through wireless communication or cable communication.

The display unit 68 displays various types of information. The display unit drive unit 66 controls display of various types of information on the display unit 68.

The operating unit 72 is used in order for a user to input an instruction relating to display of a radiation image, various types of information, or the like.

The operating unit 72 is not particularly limited, and examples of the operating unit include various types of switches, a touch panel, a touch pen, a mouse, and the like. Meanwhile, the operating unit 72 and the display unit 68 may be integrated with each other to form a touch panel display. The operation input detection unit 70 detects an operation state for the operating unit 72.

Meanwhile, in the present embodiment, various types of programs stored in the control unit 30 of the radiation imaging device 10, the control unit 40 of the console 12, and the control unit 60 of the radiation image reading device 14 are stored in the ROMs (30B, 40B, and 60B) of the control unit 30, the control unit 40, and the control unit 60 in advance, but there is no limitation thereto. Various types of programs may be stored in a recording medium such as, for example, a compact disk read only memory (CD-ROM) or a removable disk, and be installed in the ROMs (30B, 40B, and 60B) or the like from this recording medium. In addition, these programs may be installed in the ROMs (30B, 40B, and 60B) or the like from an external device through a communication line such as the Internet.

Next, the operation of the radiation imaging device 10 of the present embodiment will be described.

In a case where tomosynthesis imaging is performed, tomosynthesis imaging (capturing of a projection image) is first performed by the radiation imaging device 10 of the radiation imaging system 1 of the present embodiment.

In the radiation imaging system 1 of the present embodiment, in a case where imaging of an examinee's breast is started, a user gives an instruction for imaging start using the operating unit 52 of the console 12. The instruction of imaging start which is input by the operating unit 52 is detected by the operation input detection unit 50, and is transmitted to the radiation imaging device 10 through the I/F unit 44. In addition, the user positions an examinee's breast on the imaging surface 21 of the imaging table 20 of the radiation imaging device 10.

In the radiation imaging device 10, in a case where the instruction of imaging start of tomosynthesis imaging is received from the console 12 through the I/F unit 34, the tomosynthesis imaging is executed.

The control unit 30 of the radiation imaging device 10 causes the radiation source drive unit 36 to move the radiation source 22 to each imaging position, and causes the radiation detector 26 to capture a projection image at each imaging position. The captured projection image is stored in the storage unit 32 in association with the angle of incidence (imaging position). In addition, the projection image is transmitted to the console 12 through the I/F unit 34 in a state of being associated with the angle of incidence (imaging position). In a case where the console 12 receives a projection image or the like through the I/F unit 44, the console 12 stores the projection image or the like in the storage unit 42. A timing at which the projection image is transmitted from the radiation imaging device 10 to the console 12 is not particularly limited. For example, all the projection images may be transmitted from the radiation imaging device 10 to the console 12 after the tomosynthesis imaging is terminated, or a projection image captured every time the projection image is captured at each imaging position may be transmitted from the radiation imaging device 10 to the console 12.

In the radiation imaging system 1 of the present embodiment, the console 12 stores a series of projection images (projection images captured at all the imaging positions in one-time tomosynthesis imaging) and the angle of incidence in the storage unit 42, and then executes image processing in accordance with a user's instruction which is performed through the operating unit 52. The image processing performed by the console 12 of the present embodiment is a process of generating a first synthetic mammogram image Ms1 and three types of second synthetic mammogram images (second synthetic mammogram image Ms2 which is standard, second synthetic mammogram image Ms2h for reading calcification, and second synthetic mammogram image Ms2l for reading a tumor, which are all described later) to display the generated images on the display unit 48 of the console 12. Meanwhile, hereinafter, a case of being simply called the "second synthetic mammogram image" refers to a case of being collectively called regardless of type.

Figure 4:
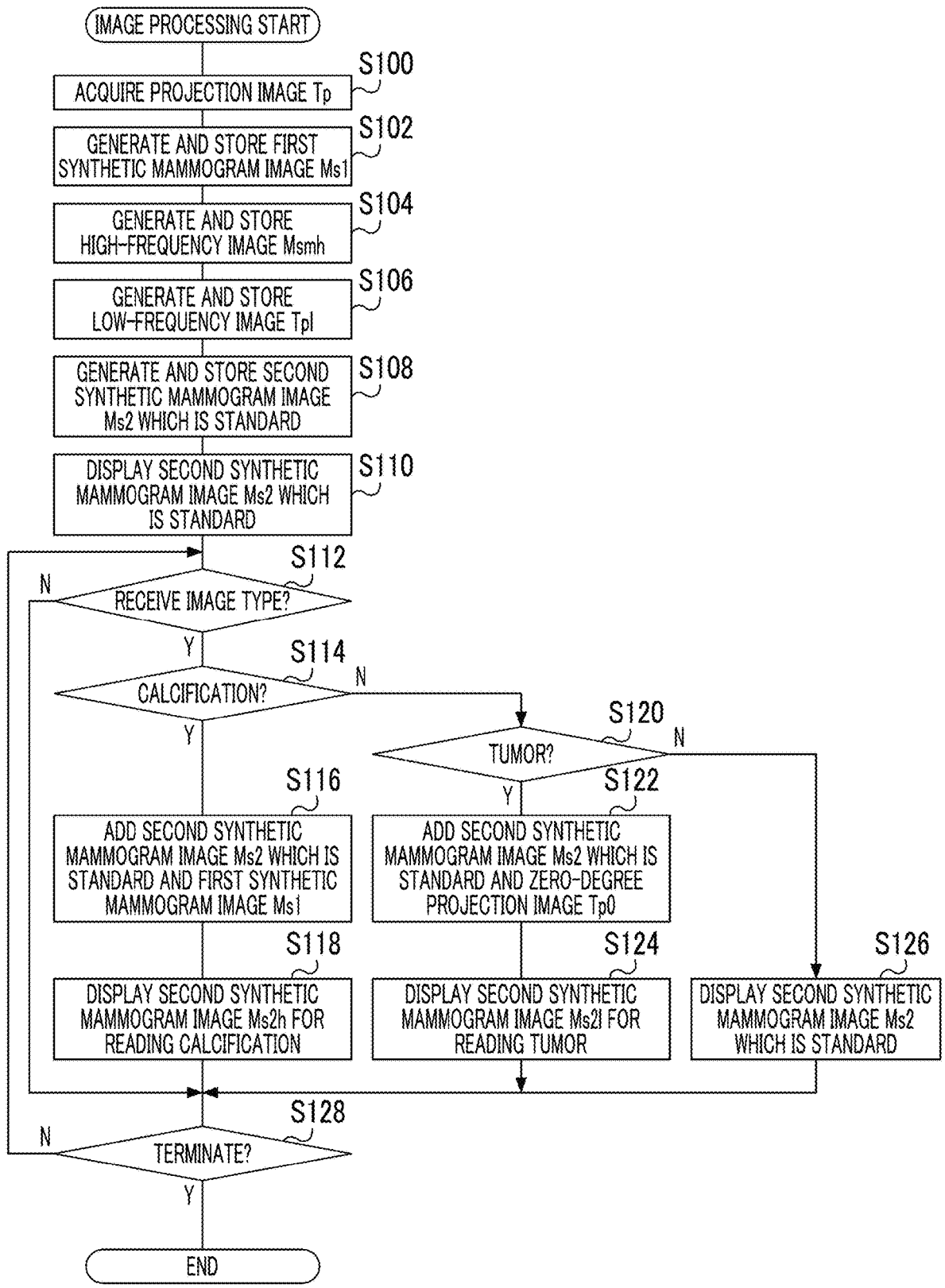
FIG. 4 is a flow diagram illustrating an example of image processing which is executed by a console of the first embodiment.

FIG. 4 shows a flow diagram illustrating an example of image processing which is executed by the control unit 40 of the console 12 of the present embodiment. In the console 12 of the present embodiment, the CPU 40A of the control unit 40 executes an image processing program stored in the ROM 40B, to thereby execute image processing shown in FIG. 4.

In step S100 of FIG. 4, the control unit 40 acquires a series of projection images Tp to be processed from the storage unit 42 by reading out the projection images. In the next step S102, the control unit 40 generates the first synthetic mammogram image Ms1, and stores the generated image in the storage unit 42.

In the present embodiment, the "first synthetic mammogram image" refers to a two-dimensional image which is generated by synthesizing a projection image Tp or a reconstructed image Tr. An example of a method of generating the first synthetic mammogram image Ms1 includes the above-described MIP method.

In the next step S104, the control unit 40 generates a high-frequency image Msmh by extracting a high-frequency component higher than a predetermined frequency from the first synthetic mammogram image Ms1 and stores the generated high-frequency image in the storage unit 42. Meanwhile, in the present embodiment, the "frequency" refers to a "spatial frequency".

Meanwhile, in the present embodiment, an image having a high-frequency component includes an image indicating calcification or focal asymmetric density (FAD), and an image having a low-frequency component includes an image indicating a tumor. Frequencies which are set to threshold values of high frequency and low frequency are stored in the storage unit 42 in advance. A specific example of the threshold value includes a frequency corresponding to a magnitude of approximately 10 mm.

A method of generating the high-frequency image Msmh is not particularly limited, and examples of the method include a method of performing a filtering process using a high-pass filter that allows passage of a high-frequency component higher than the above threshold value, a method of subtracting an image, obtained by a filtering process using a low-pass filter that allows passage of a low-frequency component lower than the above threshold value, from an image before the filtering process, and the like.

The generated high-frequency image Msmh is an image indicating a fine structure such as the contour portion of an image or calcification.

In the next step S106, the control unit 40 generates a low-frequency image Tp1 and stores the generated image in the storage unit 42.

The control unit 40 of the present embodiment generates the low-frequency image Tp1 by extracting a low-frequency component having equal to or less than the above threshold value from a projection image (hereinafter, referred to as a "zero-degree projection image") Tp0 captured at an imaging position having an angle of incidence of 0 degrees, in the projection image Tp.

A method of generating the low-frequency image Tp1 is not particularly limited, and an example of the method includes a method of performing a filtering process using a low-pass filter that allows passage of a low-frequency component having equal to or less than the above threshold value. The generated low-frequency image Tp1 is an image indicating a structure having a rough variation in density.

Figure 5A:
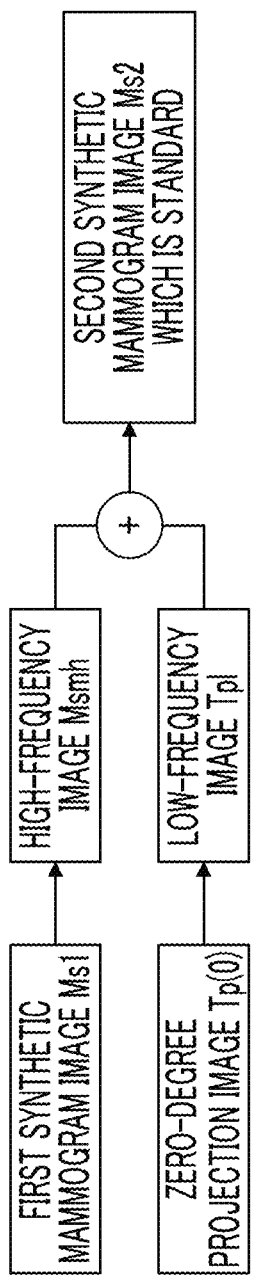
FIGS. 5A to 5C are diagrams illustrating a method of generating a second synthetic mammogram image, a second synthetic mammogram image for reading calcification, and a second synthetic mammogram image for reading a tumor of the first embodiment.

In the next step S108, the control unit 40 generates the second synthetic mammogram image Ms2 which is standard and stores the generated image in the storage unit 42. As shown in FIG. 5A, the control unit 40 of the present embodiment generates the second synthetic mammogram image Ms2 which is standard by synthesizing the high-frequency image Msmh and the low-frequency image Tp1. Meanwhile, in the following, since other types of images (for reading calcification and reading a tumor) are generated on the basis of the second synthetic mammogram image generated by the present step, the second synthetic mammogram image generated by the present step is referred to as the "second synthetic mammogram image Ms2 which is standard". In addition, in the present embodiment, the "synthesis" of an image refers to the addition of a pixel value of a pixel to which each corresponding image corresponds.

In the next step S110, the control unit 40 causes the display unit drive unit 46 to display the generated second synthetic mammogram image Ms2 which is standard on the display unit 48.

In a case where a user desires to display a second synthetic mammogram image different in type from the second synthetic mammogram image displayed on the display unit 48, the user indicates the type of second synthetic mammogram image desired to be displayed using the operating unit 52. Specifically, in a state where the second synthetic mammogram image Ms2 which is standard is displayed on the display unit 48, the user indicates the type of image, desired to be displayed on the display unit 48, out of the second synthetic mammogram image Ms2*h* for reading calcification and the second synthetic mammogram image Ms2*l* for reading a tumor, using the operating unit 52.

Consequently, in the next step S112, the control unit 40 determines whether to receive the type of image. In a case where the type of image is not received, a negative determination is made, followed by proceeding to step S128. On the other hand, in a case where the type of image is received, a positive determination is made, followed by proceeding to step S114.

In step S114, the control unit 40 determines whether the type of image received is the second synthetic mammogram image Ms2*h* for reading calcification. In a case where the second synthetic mammogram image Ms2*h* for reading calcification is received as the type of image, a positive determination is made, followed by proceeding to step S116.

Figure 5B:
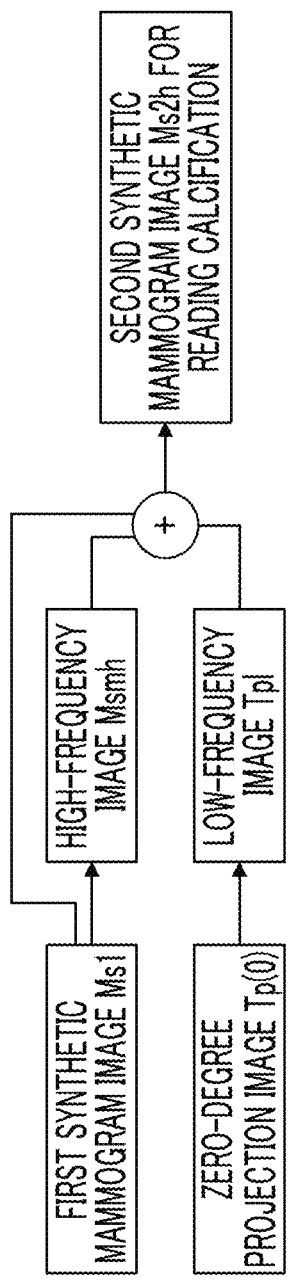

In step S116, the control unit 40 synthesizes the second synthetic mammogram image Ms2 which is standard and the first synthetic mammogram image Ms1 and generates the second synthetic mammogram image Ms2*h* for reading calcification. That is, as shown in FIG. 5B, since the high-frequency image Msmh, the low-frequency image Tp1, and the first synthetic mammogram image Ms1 are synthesized, the second synthetic mammogram image Ms2*h* for reading calcification is an image in which a high-frequency component (edge portion of the image) is highlighted, as compared with the second synthetic mammogram image Ms2 which is standard.

In the next step S118, the control unit 40 causes the display unit drive unit 46 to display the generated second synthetic mammogram image Ms2*h* for reading calcification on the display unit 48, followed by proceeding to step S128. Meanwhile, a display method herein is not limited, and the second synthetic mammogram image Ms2*h* for reading calcification may be displayed instead of the second synthetic mammogram image which is already displayed on the display unit 48, or the second mammogram image which is being displayed and the second synthetic mammogram image Ms2*h* for reading calcification may be displayed side by side.

On the other hand, in step S114, in a case where the type of image received by the control unit 40 is determined not to be for reading calcification, a negative determination is made, followed by proceeding to step S120. In step S120, the control unit 40 determines whether the type of image received is the second synthetic mammogram image Ms2*l* for reading a tumor. In a case where the second synthetic mammogram image Ms2*l* for reading a tumor is received as the type of image, a positive determination is made, followed by proceeding to step S122.

Figure 5C:
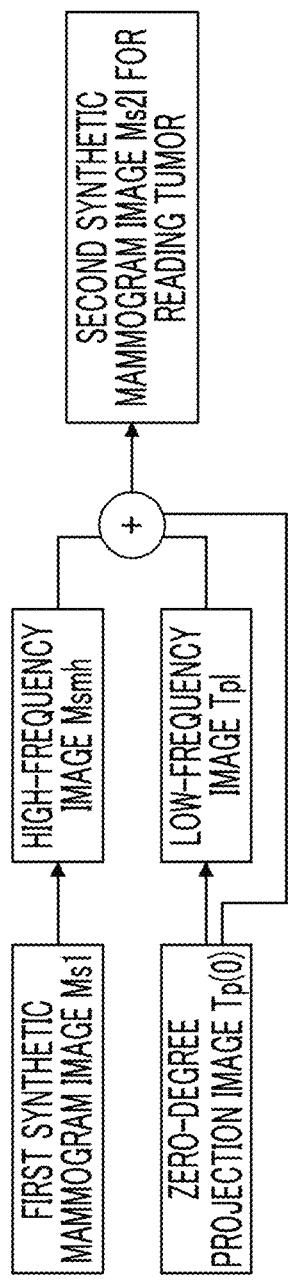

In step S122, the control unit 40 synthesizes the second synthetic mammogram image Ms2 which is standard and the zero-degree projection image Tp0 and generates the second synthetic mammogram image Ms2*l* for reading a tumor. That is, as shown in FIG. 5C, since the high-frequency image Msmh, the low-frequency image Tp1, and the zero-degree projection image Tp0 are synthesized, the second synthetic mammogram image Ms2*l* for reading a tumor changes to an image in which a low-frequency component is highlighted, as compared with the second synthetic mammogram image Ms2 which is standard.

In the next step S124, the control unit 40 causes the display unit drive unit 46 to display the generated second synthetic mammogram image Ms2*l* for reading a tumor on the display unit 48, followed by proceeding to step S128. Meanwhile, a display method herein is not limited, and the second synthetic mammogram image Ms2*l* for reading a tumor may be displayed instead of the second synthetic mammogram image which is already being displayed on the display unit 48, or the second mammogram image which is being displayed and the second synthetic mammogram image Ms2*l* for reading a tumor may be displayed side by side.

On the other hand, in step S120, in a case where the type of image received by the control unit 40 is determined not to be for reading a tumor, a negative determination is made, followed by proceeding to step S126. Meanwhile, here, a case where a negative determination is made refers to a case where the type of image received is the second synthetic mammogram image Ms2 which is standard. Therefore, in step S126, the control unit 40 causes the display unit drive unit 46 to display the second synthetic mammogram image Ms2 which is standard on the display unit 48, followed by proceeding to step S128.

In step S128, the control unit 40 determines whether to terminate the present image processing. In a case where the image processing is not terminated, a negative determination is made, followed by returning to step S112, and the above process is repeated. On the other hand, for example, in a case where a termination instruction for image processing is received from a user through the operation input detection unit 50 and the operating unit 52, or the like, a positive determination is made, and the present image processing is terminated.

Meanwhile, in the present embodiment, the second synthetic mammogram image is generated in accordance with the type of image, but the second synthetic mammogram image according to the amount of noise or the like may be generated without being limited to the type of image.

Second Embodiment

Next, a second embodiment will be described. Meanwhile, the same components as those of the radiation imaging system 1 according to the first embodiment are denoted by the same reference numerals and signs, and thus the detailed description thereof will not be given.

The configuration of a radiation imaging system 1 is the same as that of the radiation imaging system 1 (see FIGS. 1 to 3) according to the first embodiment, and thus the description thereof will not be given.

In the present embodiment, since a portion of image processing performed by the console 12 is different, different processing will be described.

In the console 12 of the present embodiment, in a case where the high-frequency image Msmh and the low-frequency image Tp1 are synthesized, these images are synthesized by making weightings of both the images different from each other, to thereby generate the second synthetic mammogram image Ms2*h* for reading calcification and the second synthetic mammogram image Ms2*l* for reading a tumor.

Figure 6:
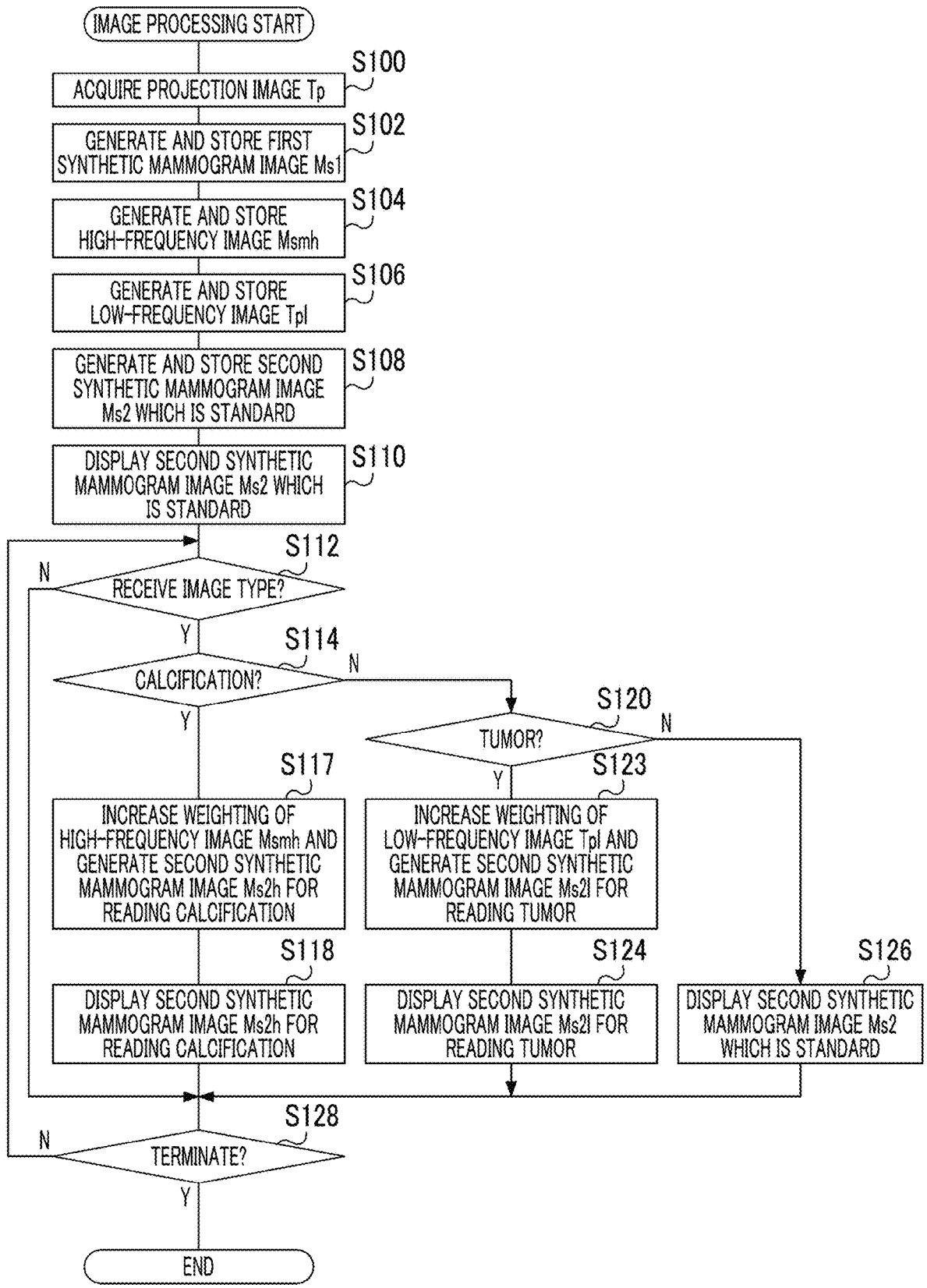
FIG. 6 is a flow diagram illustrating an example of image processing which is executed by a console of a second embodiment.

Image processing of the console 12 of the present embodiment will be described. FIG. 6 shows a flow diagram illustrating an example of image processing which is executed by the control unit 40 of the console 12 of the present embodiment.

In the image processing of the present embodiment shown in FIG. 6, steps S117 and S123 are executed instead of steps S116 and S122 of the image processing (see FIG. 4) of the first embodiment.

In the image processing of the present embodiment, in a case where the second synthetic mammogram image Ms2$h$ for reading calcification is received as the type of image (in a case where a positive determination is made in step S114), the process of step S117 is executed.

In step S117, the control unit 40 makes the weighting of the high-frequency image Msmh larger than that of the low-frequency image Tp1, and synthesizes the high-frequency image Msmh and the low-frequency image Tp1 to thereby generate the second synthetic mammogram image Ms2$h$ for reading calcification. By increasing the weighting of the high-frequency image Msmh, the second synthetic mammogram image Ms2$h$ for reading calcification changes to an image in which a high-frequency component is highlighted. Meanwhile, here, to what extent the weighting is made larger is not particularly limited, and a value, for example, experimentally obtained may be stored in the storage unit 42 in advance as weighting.

On the other hand, in a case where the second synthetic mammogram image Ms2$l$ for reading a tumor is received as the type of image (in a case where a positive determination is made in step S120), the process of step S123 is executed.

In step S123, the control unit 40 makes the weighting of the low-frequency image Tp1 larger than that of the high-frequency image Msmh, and synthesizes the high-frequency image Msmh and the low-frequency image Tp1 to thereby generate the second synthetic mammogram image Ms2$l$ for reading a tumor. By increasing the weighting of the low-frequency image Tp1, the second synthetic mammogram image Ms2$l$ for reading a tumor changes to an image in which a low-frequency component is highlighted. Meanwhile, here, to what extent the weighting is made larger is not particularly limited, and a value, for example, experimentally obtained may be stored in the storage unit 42 in advance as weighting. In addition, the weighting performed on the high-frequency image Msmh in step S117 and the weighting performed on the low-frequency image Tp1 in step S123 may be the same value, and may be different from each other.

In this manner, the console 12 of the present embodiment makes the weighting of the high-frequency image Msmh larger than that of the low-frequency image Tp1 and synthesizes the high-frequency image Msmh and the low-frequency image Tp1, to thereby generate the second synthetic mammogram image Ms2$h$ for reading calcification. In addition, the console 12 makes the weighting of the low-frequency image Tp1 larger than that of the high-frequency image Msmh and synthesizes the high-frequency image Msmh and the low-frequency image Tp1, to thereby generate the second synthetic mammogram image Ms2$l$ for reading a tumor.

Meanwhile, in the above, the second synthetic mammogram image Ms2$h$ for reading calcification and the second synthetic mammogram image Ms2$l$ for reading a tumor are generated using weighting which is set in advance, but weighting may be able to be set by a user.

Figure 7:
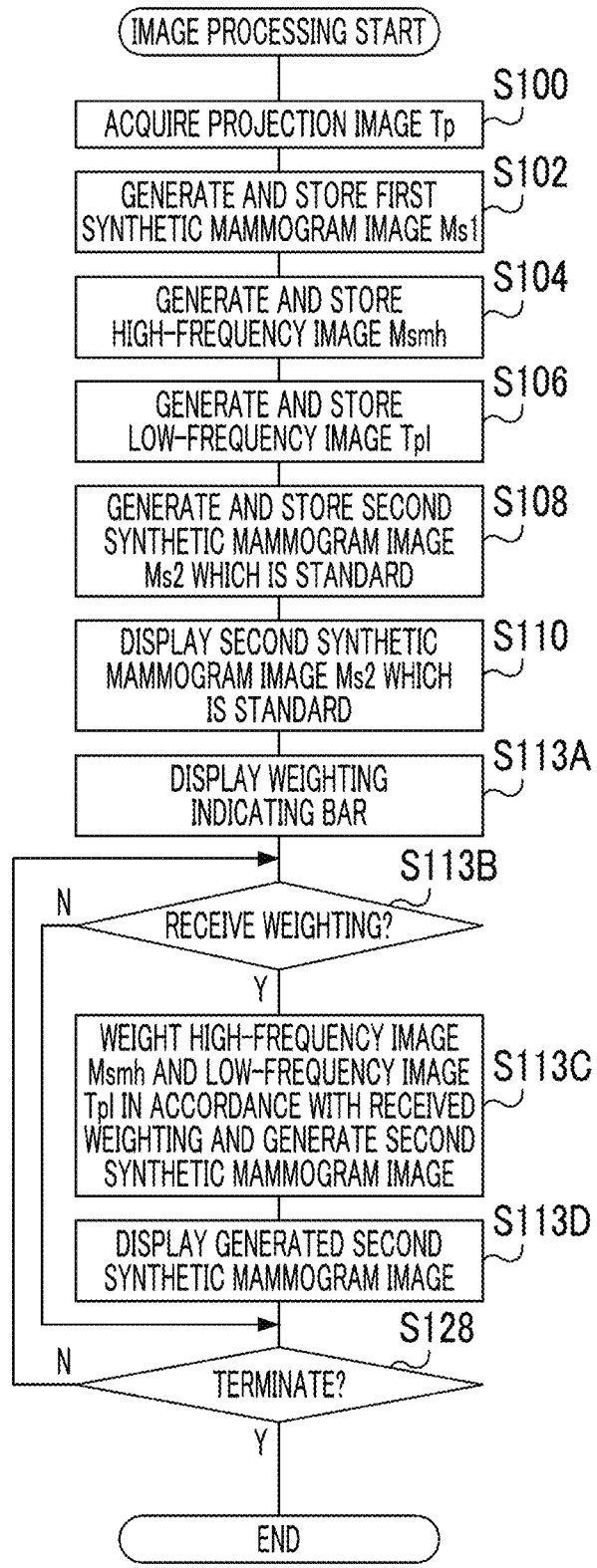
FIG. 7 is a flow diagram illustrating an example of image processing in a case where a user sets weighting.

FIG. 7 shows a flow diagram illustrating an example of image processing in a case where a user sets weighting. In the image processing shown in FIG. 7, steps S113A to S113D are executed instead of steps S112 to S126 of the image processing shown in FIG. 6 described above. In the image processing shown in FIG. 7, in step S110, the control unit 40 displays the second synthetic mammogram image Ms2 which is standard on the display unit 48, followed by proceeding to step S113A.

Figure 8:
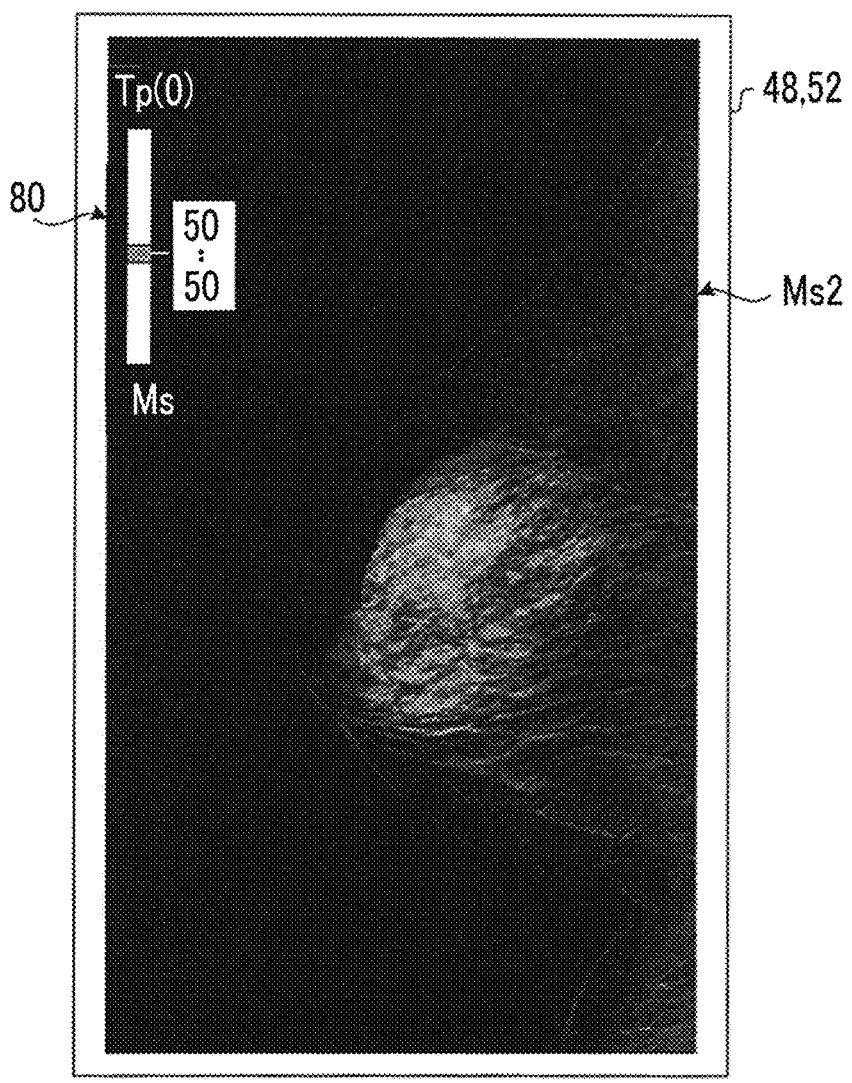
FIG. 8 is a diagram illustrating a display example of a weighting indicating bar.

In step S113A, the control unit 40 displays a weighting indicating bar on the display unit 48. FIG. 8 shows a diagram illustrating a display example of a weighting indicating bar 80. The display example shown in FIG. 8 shows a state where the weighting indicating bar 80 is displayed on the second synthetic mammogram image Ms2 which is standard. In a case where the weighting indicating bar 80 is moved to the "Tp0" side by a user's operation, the control unit 40 makes the weighting of the low-frequency image Tp1 relatively large in accordance with the amount of movement. On the other hand, in a case where the weighting indicating bar 80 is moved to the "Ms" side by a user's operation, the control unit 40 makes the weighting of the high-frequency image Msmh relatively large in accordance with the amount of movement.

Consequently, in the next step S113B, the control unit 40 determines whether to receive weighting. Specifically, in a case where the operation of the weighting indicating bar 80 is detected by the operation input detection unit 50, a positive determination is made, followed by proceeding to step S113C.

In step S113C, the control unit 40 weights and synthesizes the high-frequency image Msmh and the low-frequency image Tp1 in accordance with the received weighting, to thereby generate the second synthetic mammogram image.

In the next step S113D, the control unit 40 displays the generated second synthetic mammogram image Ms2 on the display unit 48, followed by proceeding to step S128.

On the other hand, in a case where the weighting is not received in step S113B, a negative determination is made, followed by proceeding to step S128.

In addition, in the image processing of the present embodiment, a negative determination in step S128 is followed by proceeding to step S113B.

In this manner, a user indicates weighting, and thus an image according to the user's desire can be synthesized.

Meanwhile, in the present embodiment, a case has been described in which the weighting indicating bar 80 is displayed on the display unit 48, and a user indicates weighting by the user operating the weighting indicating bar 80, but it goes without saying that a method of indicating weighting is not limited thereto. For example, a user may indicate a specific numerical value as weighting using the operating unit 52.

Third Embodiment

Next, a third embodiment will be described. Meanwhile, the same components as those of the radiation imaging system 1 according to the first embodiment are denoted by the same reference numerals and signs, and thus the detailed description thereof will not be given.

The configuration of a radiation imaging system 1 is the same as that of the radiation imaging system 1 (see FIGS. 1 to 3) of the first embodiment, and thus the description thereof will not be given.

In the present embodiment, since a portion of image processing performed by the console 12 is different, different processing will be described. Meanwhile, in the present embodiment, the console 12 functions as an example of a frequency receiving unit of the present invention.

In the console 12 of the present embodiment, frequencies which are set to threshold values of the high-frequency image Msmh and the low-frequency image Tp1 are made variable, and the second synthetic mammogram image Ms2 which is standard is generated.

Figure 9:
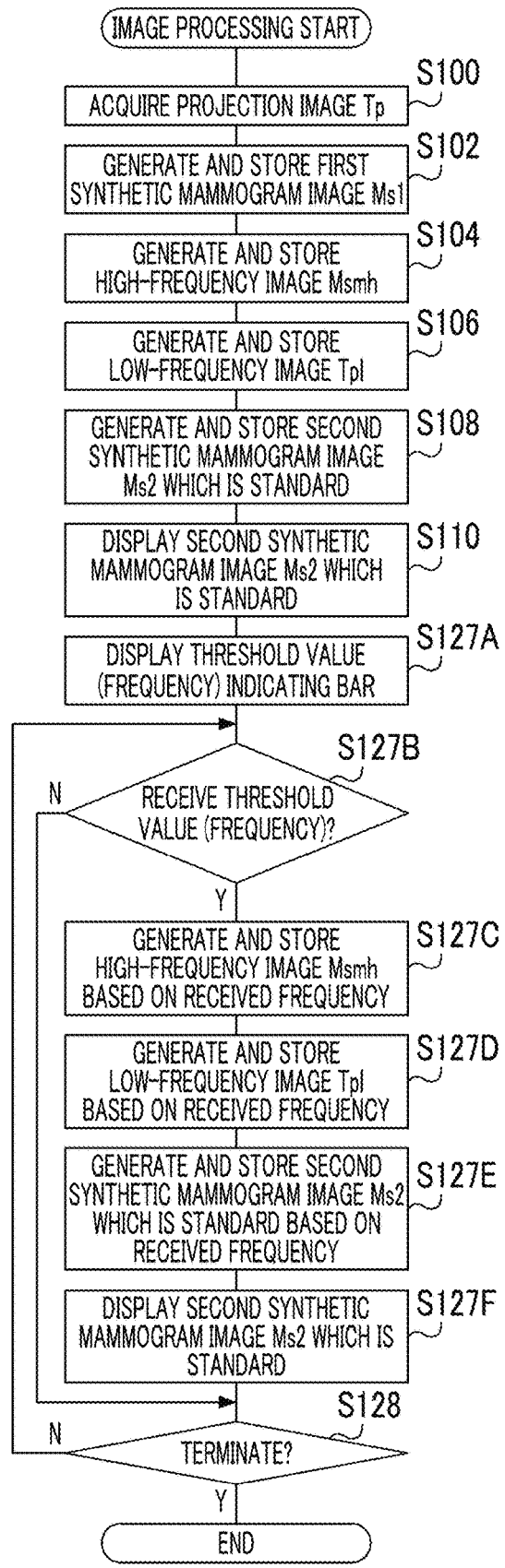
FIG. 9 is a flow diagram illustrating an example of image processing which is executed by a console of a third embodiment.

Image processing of the console 12 of the present embodiment will be described. FIG. 9 shows a flow diagram illustrating an example of image processing which is executed by the control unit 40 of the console 12 of the present embodiment. In the image processing of the present embodiment, steps S127A to S127F are executed instead of steps S112 to S126 of the image processing (see FIG. 4) of the first embodiment. In the image processing shown in FIG. 9, in step S110, the control unit 40 displays the second synthetic mammogram image Ms2 which is standard on the display unit 48, followed by proceeding to step S127A.

In step S127A, the control unit 40 displays a threshold value (frequency) indicating bar on the display unit 48. A method of displaying a threshold value (frequency) indicating bar may be performed similarly to that of the weighting indicating bar 80 described in the third embodiment. Meanwhile, it goes without saying that a method of allowing a user to indicate a frequency is not limited thereto. For example, a user may indicate a specific numerical value as a frequency using the operating unit 52.

In the next step S127B, the control unit 40 determines whether to receive a frequency. Specifically, in a case where the operation of a frequency indicating bar is detected by the operation input detection unit 50, a positive determination is made, followed by proceeding to step S127C.

In step S127C, the control unit 40 generates the high-frequency image Msmh from the first synthetic mammogram image Ms1 similarly to step S104 described above on the basis of the received frequency, and stores the generated image in the storage unit 42.

In the next step S127D, the control unit 40 generates the low-frequency image Tp1 from the zero-degree projection image Tp0 similarly to step S106 described above on the basis of the received frequency, and stores the generated image in the storage unit 42.

In the next step S127E, the control unit 40 generates the second synthetic mammogram image Ms2 which is standard, similarly to step S108 described above.

In the next step S127F, the control unit 40 displays the generated second synthetic mammogram image Ms2 which is standard on the display unit 48, followed by proceeding to step S128.

On the other hand, in a case where the frequency is not received in step S127B, a negative determination is made, followed by proceeding to step S128.

In this manner, the console 12 of the present embodiment can synthesize an image according to a user's desire by the user indicating the threshold values (frequencies) of the high-frequency image Msmh and the low-frequency image Tp1. Thereby, a threshold value can be indicated in accordance with the size of an object of interest which is desired to be read by the user.

Meanwhile, in the present embodiment, a case where a frequency is received has been described, but information for specifying a frequency rather than the value of the frequency itself may be received. The information for specifying a frequency is not particularly limited, and examples thereof include a sign or the like indicating a choice in a case where a plurality of frequencies and choices are associated with each other in advance, the size or coefficient of a filter for generating the high-frequency image Msmh or the low-frequency component of the low-frequency image Tp1, and the like.

As described above, the control unit 40 of the console 12 of each of the embodiments sets the angle of incidence of radiation, which is emitted from the radiation source 22, is transmitted through a breast, and is incident on the detection surface 27 of the radiation detector 26 provided on the opposite side to the radiation source 22 with the breast interposed therebetween with respect to the detection surface 27, to a plurality of angles different from each other including an angle (0 degrees) in a normal direction of the detection surface 27, and acquires at least one of a plurality of projection images captured by the radiation detector 26 in accordance with the angle of incidence or reconstructed images reconstructed using the projection images. In addition, the control unit 40 generates the first synthetic mammogram image Ms1 on the basis of any one of the plurality of the projection images or the reconstructed images. In addition, the control unit 40 generates the second synthetic mammogram image Ms2 which is standard by synthesizing the high-frequency image Msmh having a high-frequency component higher than a predetermined frequency of the first synthetic mammogram image Ms1 and the low-frequency image Tp1 having a low-frequency component of equal to or lower than a predetermined frequency of the zero-degree projection image Tp0.

Figure 10:
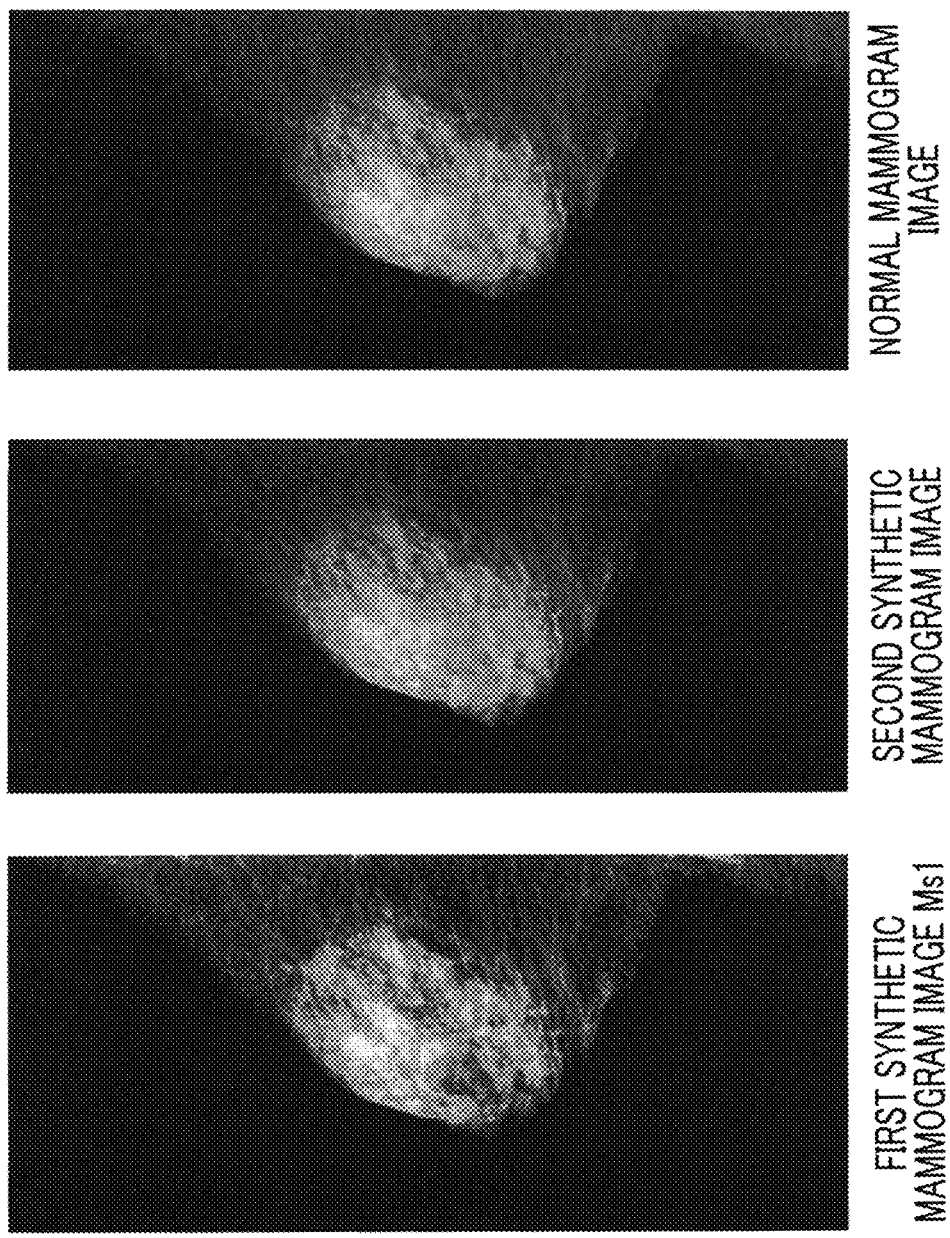
FIG. 10 is a diagram illustrating specific examples of a first synthetic mammogram image, a second synthetic mammogram image, and a normal mammogram image which are generated by a MIP method.

In a case where the first synthetic mammogram image Ms1 is generated using the MIP method, information of a pixel value between pixels is lost by generating a synthetic mammogram image using information of a structure which is not present on the same cross-section. For this reason, a difference between pixel values within the surface of the first synthetic mammogram image Ms1 may become smaller than in a normal mammogram image (radiation image captured with the direction of incidence set to be only in a normal direction). FIG. 10 shows specific examples of the first synthetic mammogram image Ms1, the second synthetic mammogram image Ms2 which is standard, and the normal mammogram image which are generated using the MIP method.

The density of a normal mammary gland becoming darker from the nipple side toward the wall of the chest sometimes becomes lighter on the flat or chest-wall side, in the first synthetic mammogram image Ms1. In such a case, it is difficult to discriminate between the normal mammary gland and the lesion such as FAD. For this reason, in the first synthetic mammogram image Ms1 shown in FIG. 10, light and shade information is not appropriately shown as compared with the normal mammogram image. On the other hand, as shown in FIG. 10, in the second synthetic mammogram image, light and shade information is shown similarly to the normal mammogram image.

The console 12 of each of the embodiments generates the second synthetic mammogram image by synthesizing the high-frequency image Msmh which is a high-frequency component of the first synthetic mammogram image Ms1 and the low-frequency image Tp1 which is a low-frequency component of the zero-degree projection image Tp0. The zero-degree projection image Tp0 is a radiation image captured with the direction of incidence set only to a normal direction, similarly to the normal mammogram image. Since the low-frequency image Tp1 generated from the zero-degree projection image Tp0 is used as a low-frequency component, the second synthetic mammogram image is a radiation image showing light and shade information appropriately.

In addition, since the high-frequency image Msmh generated from the first synthetic mammogram image Ms1 is used as a high-frequency component, the second synthetic mammogram image is a radiation image which is less in noise than the first synthetic mammogram image Ms1.

Therefore, according to the console 12 of the present embodiment, it is possible to improve the image quality of a synthetic mammogram image.

In addition, according to each of the embodiments, since the second synthetic mammogram image can be used similarly to the normal mammogram image, imaging for capturing the normal mammogram image may not be performed separately from tomosynthesis imaging. Therefore, it is possible to reduce an examinee's amount of exposure.

Meanwhile, in the first and second embodiments, a case has been described where frequencies at which an image including an image indicating calcification is set to an image of a high-frequency component, and an image including an image indicated by a tumor is set to an image of a low-frequency component are set to threshold values, but frequencies which are set to threshold values are not limited thereto. For example, frequencies at which an image including a fine structure embedded in random noise in the zero-degree projection image Tp0 is set to a high-frequency image, and an image including other large structures is set to a low-frequency image may be set to threshold values.

Figure 11:
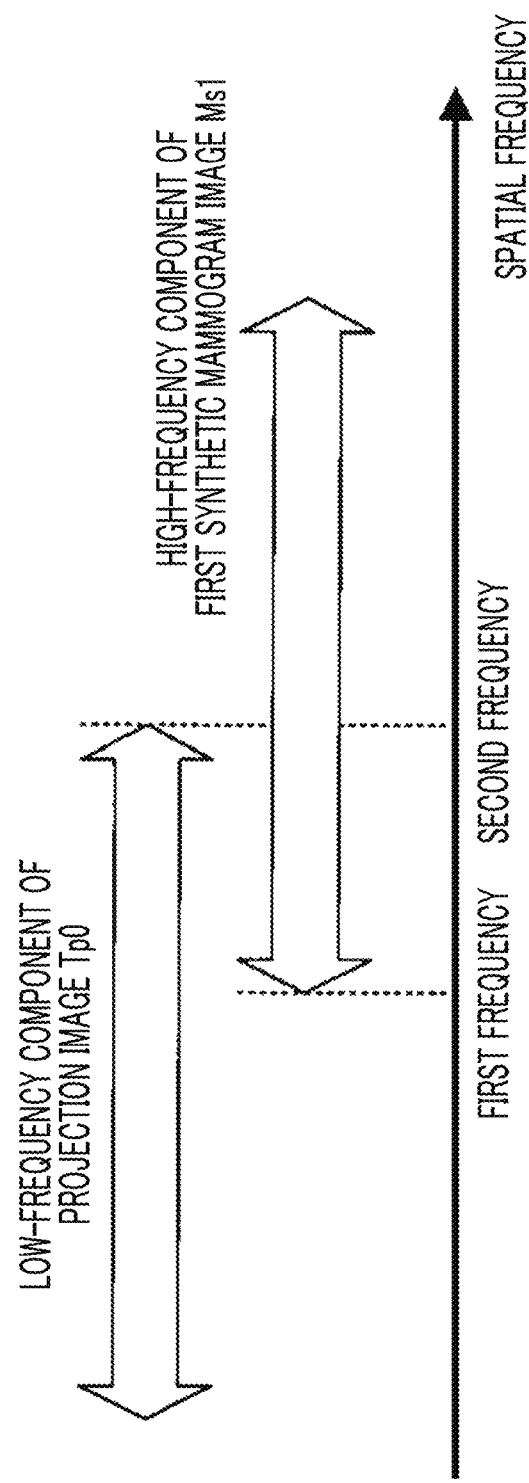
FIG. 11 is a diagram illustrating a frequency which is set to a threshold value.

In addition, in each of the embodiments, a case has been described in which predetermined frequencies are set to a first frequency and a second frequency of the present invention, as an example, and the predetermined frequencies are set to threshold values, but frequencies (first frequency and second frequency) which are set to threshold values are not limited thereto. For example, as shown in FIG. 11, the second frequency may be higher than the first frequency (first frequency<second frequency).

Meanwhile, in each of the embodiments, a case has been described in which the second synthetic mammogram image Ms2 which is standard is initially displayed on the display unit 48, and then the second synthetic mammogram image according to a user's instruction is displayed, but the second synthetic mammogram image according to a user's instruction may be displayed from the beginning.

Meanwhile, in each of the embodiments, a case has been described in which the console 12 has a function as the image processing device of the present invention, but the radiation image reading device 14 may have a function as the image processing device. In addition, the radiation imaging device 10, the console 12, and the radiation image reading device 14 may have some or all of the functions of the respective units of the acquisition unit, the first generation unit, the second generation unit, the receiving unit, and the frequency receiving unit.

Meanwhile, the radiation R in each of the embodiments is particularly limited, and X-rays, y-ray or the like can be applied.

Besides, the configurations, operations and the like of the radiation imaging system 1, the radiation imaging device 10, the console 12, and the like described in each of the embodiments are an example, and it goes without saying that changes and modifications can be made, depending on the situation, without departing from the spirit and scope of the present invention.

EXPLANATION OF REFERENCES

1: radiation imaging system
10: radiation imaging device
12: console
22: radiation source
26: radiation detector
27: detection surface
40, 60: control unit

What is claimed is:

1. An image processing device comprising:
an acquisition unit that sets an angle of incidence of radiation, which is emitted from a radiation source, is transmitted through a subject, and is incident on a detection surface of a radiation detector with respect to the detection surface, to a plurality of angles different from each other including an angle in a normal direction of the detection surface, and acquires at least one of a plurality of projection images captured by the radiation detector in accordance with the angle of incidence or reconstructed images reconstructed using the projection images;
a first generation unit that generates a first synthetic mammogram image on the basis of any one of the plurality of the projection images or the reconstructed images; and
a second generation unit that generates a second synthetic mammogram image by synthesizing an image of a high-frequency component higher than a first spatial frequency of the first synthetic mammogram image and an image of a low-frequency component of equal to or lower than a second spatial frequency of a projection image, the projection image is one of the plurality of the projection images and captured with the angle of incidence set to be in the normal direction.

2. The image processing device according to claim 1, wherein the second generation unit further synthesizes the second synthetic mammogram image and the first synthetic mammogram image.

3. The image processing device according to claim 1, further comprising a receiving unit that receives a type of image obtained by synthesis,
wherein in a case where the type of image received by the receiving unit is a calcification reading image or a high-frequency component enhanced image, the second generation unit further synthesizes the second synthetic mammogram image and the first synthetic mammogram image.

4. The image processing device according to claim 1, wherein the second generation unit further synthesizes the second synthetic mammogram image and the projection image captured with the angle of incidence set to be in the normal direction.

5. The image processing device according to claim 1, further comprising a receiving unit that receives a type of image obtained by synthesis,
wherein in a case where the type of image received by the receiving unit is a tumor reading image or a low-frequency component enhanced image, the second generation unit further synthesizes the second synthetic mammogram image and the projection image captured with the angle of incidence set to be in the normal direction.

6. The image processing device according to claim 1, wherein the second generation unit performs synthesis by performing weighting on each of an image of a high-frequency component of the first synthetic mammogram image and an image of a low-frequency component of the projection image.

7. The image processing device according to claim 2, wherein the second generation unit performs synthesis by performing weighting on each of an image of a high-frequency component of the first synthetic mammogram image and an image of a low-frequency component of the projection image.

8. The image processing device according to claim 3, wherein the second generation unit performs the synthesis by performing weighting on each of an image of a high-frequency component of the first synthetic mammogram image and an image of a low-frequency component of the projection image.

9. The image processing device according to claim 4, wherein the second generation unit performs synthesis by performing weighting on each of an image of a high-frequency component of the first synthetic mammogram image and an image of a low-frequency component of the projection image.

10. The image processing device according to claim 5, wherein the second generation unit performs the synthesis by performing weighting on each of an image of a high-frequency component of the first synthetic mammogram image and an image of a low-frequency component of the projection image.

11. The image processing device according to claim 1, further comprising a frequency receiving unit that receives an input of information for specifying at least one of the first spatial frequency or the second spatial frequency.

12. The image processing device according to claim 2, further comprising a frequency receiving unit that receives an input of information for specifying at least one of the first spatial frequency or the second spatial frequency.

13. The image processing device according to claim 3, further comprising a frequency receiving unit that receives an input of information for specifying at least one of the first spatial frequency or the second spatial frequency.

14. The image processing device according to claim 4, further comprising a frequency receiving unit that receives an input of information for specifying at least one of the first spatial frequency or the second spatial frequency.

15. The image processing device according to claim 5, further comprising a frequency receiving unit that receives an input of information for specifying at least one of the first spatial frequency or the second spatial frequency.

16. The image processing device according to claim 6, further comprising a frequency receiving unit that receives an input of information for specifying at least one of the first spatial frequency or the second spatial frequency.

17. The image processing device according to claim 1, wherein the first spatial frequency is lower than the second spatial frequency, or the first spatial frequency and the second spatial frequency are equal to each other.

18. A radiation imaging system comprising:
a radiation imaging device including a radiation source and a radiation detector provided on an opposite side to the radiation source with a subject interposed therebetween; and
the image processing device according to claim 1.

19. An image processing method comprising causing a computer to execute:
setting an angle of incidence of radiation, which is emitted from a radiation source, is transmitted through a subject, and is incident on a detection surface of a radiation detector with respect to the detection surface, to a plurality of angles different from each other including an angle in a normal direction of the detection surface, and acquiring at least one of a plurality of projection images captured by the radiation detector in accordance with the angle of incidence or reconstructed images reconstructed using the projection images;
generating a first synthetic mammogram image on the basis of any one of the plurality of the projection images or the reconstructed images; and
generating a second synthetic mammogram image by synthesizing an image of a high-frequency component higher than a first spatial frequency of the first synthetic mammogram image and an image of a low-frequency component of equal to or lower than a second spatial frequency of a projection image, the projection image is one of the plurality of the projection images and captured with the angle of incidence set to be in the normal direction.

20. A non-transitory computer readable recording medium storing an image processing program for causing a computer to execute:
setting an angle of incidence of radiation, which is emitted from a radiation source, is transmitted through a subject, and is incident on a detection surface of a radiation detector with respect to the detection surface, to a plurality of angles different from each other including an angle in a normal direction of the detection surface, and acquiring at least one of a plurality of projection images captured by the radiation detector in accordance with the angle of incidence or reconstructed images reconstructed using the projection images;
generating a first synthetic mammogram image on the basis of any one of the plurality of the projection images or the reconstructed images; and
generating a second synthetic mammogram image by synthesizing an image of a high-frequency component higher than a first spatial frequency of the first synthetic mammogram image and an image of a low-frequency component of equal to or lower than a second spatial frequency of a projection image, the projection image is one of the plurality of the projection images and captured with the angle of incidence set to be in the normal direction.

* * * * *